(12) United States Patent
Ide (10) Patent No.: US 11,399,703 B2
(45) Date of Patent: Aug. 2, 2022

(54) ENDOSCOPE

(71) Applicant: OLYMPUS CORPORATION, Tokyo (JP)

(72) Inventor: Yuka Ide, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 467 days.

(21) Appl. No.: 16/402,745

(22) Filed: May 3, 2019

(65) Prior Publication Data

US 2019/0254504 A1    Aug. 22, 2019

Related U.S. Application Data

(63) Continuation of application No. PCT/JP2017/029907, filed on Aug. 22, 2017.

(30) Foreign Application Priority Data

Jan. 13, 2017   (JP) .............................. JP2017-004223

(51) Int. Cl.
*A61B 1/005* (2006.01)
*A61B 1/00* (2006.01)
(Continued)

(52) U.S. Cl.
CPC ............ *A61B 1/0057* (2013.01); *A61B 1/005* (2013.01); *A61B 1/0008* (2013.01);
(Continued)

(58) Field of Classification Search
CPC ....... A61B 1/0057; A61B 1/018; A61B 1/005; A61B 1/0008; A61B 1/0055; A61B 1/04;
(Continued)

(56) References Cited

U.S. PATENT DOCUMENTS

2006/0264708 A1* 11/2006 Horne, Jr. .............. A61B 1/018
600/130

FOREIGN PATENT DOCUMENTS

JP     H05-020701 U     3/1993
JP     H06-269400 A     9/1994
(Continued)

OTHER PUBLICATIONS

International Search Report dated Oct. 3, 2017 issued in PCT/JP2017/029907.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

The endoscope of the invention includes: an insertion portion; a multi-lumen tube including bending operation wire insertion holes; bending operation wires inserted into the bending operation wire insertion holes; a wire retaining member including two opening portions; a pressing member that presses a distal end surface of the multi-lumen tube through the wire retaining member; a treatment instrument insertion channel; a distal end rigid member including a through hole; and a pipe member. A contact area of the wire retaining member with a distal end surface of the multi-lumen tube is set to be larger than a contact area of a pressing member with the wire retaining member. The pressing member is disposed between the two opening portions of the wire retaining member. The wire retaining member includes a pipe holding portion that holds the pipe member and is held between the distal end rigid member and the multi-lumen tube.

5 Claims, 6 Drawing Sheets (51) Int. Cl.
*A61M 25/01* (2006.01)
*G02B 23/24* (2006.01)
*A61B 1/018* (2006.01)
*A61B 1/04* (2006.01)
*A61B 1/06* (2006.01)

(52) U.S. Cl.
CPC ............ *A61B 1/0055* (2013.01); *A61B 1/018* (2013.01); *A61M 25/0147* (2013.01); *G02B 23/24* (2013.01); *G02B 23/2476* (2013.01); *A61B 1/04* (2013.01); *A61B 1/0676* (2013.01)

(58) Field of Classification Search
CPC ..... A61B 1/0676; A61B 1/0011; G02B 23/24; G02B 23/2476; G02B 23/2423; A61M 25/0147
USPC ........................................................ 600/146
See application file for complete search history.

(56) References Cited

FOREIGN PATENT DOCUMENTS

| | | | |
|---|---|---|---|
| JP | H08-094941 A | | 4/1996 |
| JP | H09-108173 A | | 4/1997 |
| JP | H09108173 A | * | 4/1997 |
| JP | 11267095 A | * | 10/1999 |
| JP | H11-267095 A | | 10/1999 |
| JP | 2006149844 A | * | 6/2006 |
| JP | 2006-340878 A | | 12/2006 |
| JP | 2006340878 A | * | 12/2006 |
| JP | 2009247550 A | * | 10/2009 |

\* cited by examiner

ENDOSCOPE

CROSS REFERENCE TO RELATED APPLICATION

This application is a continuation application of PCT/JP2017/029907 filed on Aug. 22, 2017 and claims benefit of Japanese Application No. 2017-004223 filed in Japan on Jan. 13, 2017, the entire contents of which are incorporated herein by this reference.

BACKGROUND OF THE INVENTION

1. Field of the Invention

The present invention relates to an endoscope including a bending portion configured by using a multi-lumen tube.

2. Description of the Related Art

Conventionally, endoscopes including an elongated tubular insertion portion have been widely used, for example, in medical fields, industrial fields, etc.

Among such endoscopes, a medical endoscope for use in the medical fields is configured to be capable of observing organs and the like by inserting an insertion portion into a body cavity of a living body, for example, and capable of performing, as needed, various kinds of treatment on the organs and the like by using a treatment instrument inserted into a treatment instrument insertion channel provided in the endoscope. In addition, an endoscope for use in the industrial fields is configured to insert an insertion portion into an apparatus or a machine unit such as a jet engine or a pipe in a factory, for example, to thereby be capable of observing and inspecting states of flaw, corrosion, and the like in the apparatus or the machine unit.

With regard to such conventional endoscopes of the above-described types, in order to improve the insertion performance of the insertion portion into a subject or an object, an endoscope provided with a bending portion which has pliability or flexibility and which is formed to be bendable has been put into practical use.

Various types of bending portions in conventional endoscopes have been proposed and widely put into practical use. As a configuration of such bending portions, for example, Japanese Patent Application Laid-Open Publication No. 6-269400 discloses a bending portion including a bending tube having a mechanism in which a plurality of bending pieces adjacent to each other are rotatably coupled to form a tubular shape and a plurality of bending operation wires whose distal ends are fixed to the distal end part of the bending tube, and the bending portion is configured such that the bending tube is bendable in up/down directions or left/right directions by pulling or relaxing at least one of the plurality of bending operation wires by a predetermined operation of an operation member provided at an operation portion.

Furthermore, in recent years, various proposals have been made for configurations of bending portions of endoscopes. For example, a bending portion configured by using a flexible tubular member such as a multi-lumen tube is disclosed by Japanese Patent Application Laid-Open Publication No. 8-94941, Japanese Utility Model Application Laid-Open Publication No. 5-20701, etc.

Each of the endoscopes disclosed in the Japanese Patent Application Laid-Open Publication No. 8-94941, the Japanese Utility Model Application Laid-Open Publication No. 5-20701, etc., has a configuration in which a distal end rigid member is provided on the distal end side of the bending portion configured by the multi-lumen tube, and the distal ends of the bending operation wires are fixed to the distal end rigid member.

SUMMARY OF THE INVENTION

An endoscope according to one aspect of the present invention includes: an insertion portion configured to be inserted into a subject and including a bending portion; a multi-lumen tube that forms at least the bending portion of the insertion portion, the multi-lumen tube including two bending operation wire insertion holes passing through the multi-lumen tube in a direction of a longitudinal axis; bending operation wires inserted respectively into the two bending operation wire insertion holes; a wire retaining member that is in contact with a distal end surface of the multi-lumen tube, the wire retaining member including two opening portions from which the bending operation wires are respectively drawn out; a pressing member including a fixation portion fixed to the bending operation wires and a contact portion that is in contact with the wire retaining member, the pressing member being configured to press a distal end surface of the multi-lumen tube through the wire retaining member when one of the bending operation wires is pulled; a treatment instrument insertion channel provided on a proximal end side of the wire retaining member, the treatment instrument insertion channel communicating with the multi-lumen tube in the direction of the longitudinal axis; a distal end rigid member provided on a distal end side of the wire retaining member, and including a through hole; and a pipe member including one end inserted into the treatment instrument insertion channel and another end inserted into the through hole of the distal end rigid member, the pipe member being configured to allow the treatment instrument insertion channel and the through hole of the distal end rigid member to communicate with each other. A contact area of the wire retaining member with the distal end surface of the multi-lumen tube is set to be larger than a contact area of the contact portion with the wire retaining member. The pressing member is disposed between the two opening portions of the wire retaining member. The wire retaining member includes a pipe holding portion configured to hold the pipe member, and the wire retaining member is held between the distal end rigid member and the multi-lumen tube.

DETAILED DESCRIPTION OF THE PREFERRED EMBODIMENT(S)

Hereinafter, the present invention will be described with reference to drawings. The drawings used for describing the embodiments below are schematic drawings, and there is a case where a different dimensional relationship and a different scale size are used for each of the constituent elements in order to allow each of the constituent elements to be illustrated in a recognizable size in the drawings. Therefore, the present invention is not limited only to the embodiments shown in the drawings regarding the number, shapes, ratio of the sizes of the constituent elements, a relative positional relationship among the constituent elements, etc.

First Embodiment

Figure 1:
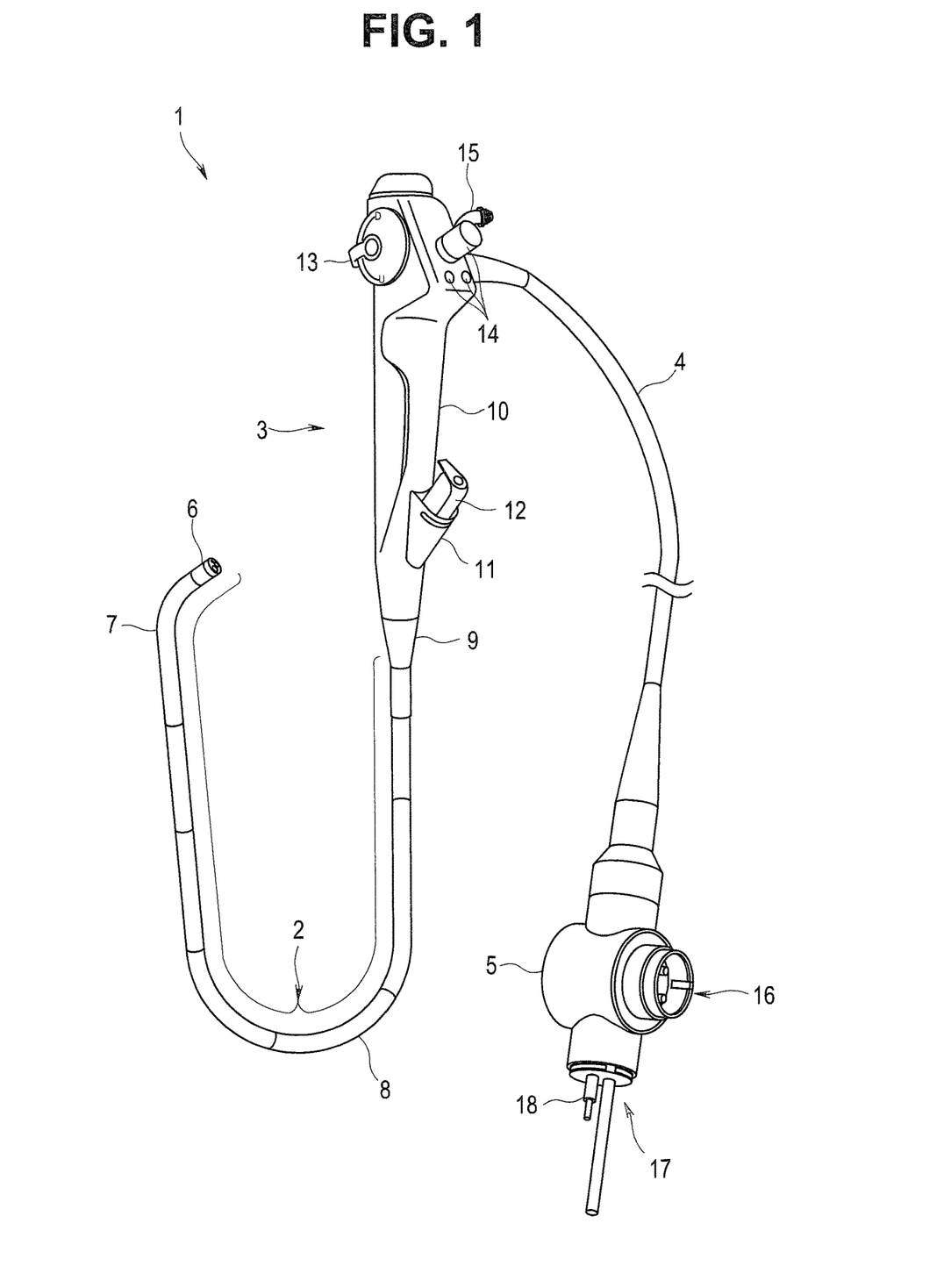
FIG. 1 is a whole perspective view showing a schematic configuration of an endoscope according to a first embodiment of the present invention.

First, description will be made below on a schematic configuration of an endoscope according to the first embodiment of the present invention, with reference to FIG. 1. FIG. 1 is a whole perspective view showing the schematic configuration of an endoscope according the first embodiment of the present invention.

An endoscope 1 according to the first embodiment of the present invention mainly includes an insertion portion 2, an operation portion 3, a universal cord 4, an endoscope connector 5, etc.

The insertion portion 2 is a tubular member formed in an elongated tubular shape and configured to be inserted in a subject. The insertion portion 2 is formed by including continuously, in the following order from the distal end side, a distal end portion 6, a bending portion 7, and a flexible tube portion 8. The insertion portion 2 has flexibility as a whole.

Among the above-described elements, the distal end portion 6 includes an image pickup unit (not shown) as an image pickup apparatus including inside thereof an image pickup device, etc., and an illumination unit (not shown) configured to emit illumination light forward.

Note that a type of an endoscope to which the present invention is applicable is not limited to the above-described example (electronic endoscope including an image pickup unit, etc.), and may be another type, what is called, a fiber scope that does not include an image pickup unit and includes an image guide fiber in the insertion portion 2, for example.

The bending portion 7 is a mechanism unit configured to be capable of actively bending in two directions, i.e., up and down directions (UP and DOWN) in response to the rotation operation of a bending lever 13 for performing bending operation. The bending lever 13 is one of the operation members (to be described later) provided on the operation portion 3.

Note that the configuration of the bending portion in the endoscope to which the present invention is applicable is not limited to the above-described one (the type bendable in two directions, i.e., up and down directions), but may be a configuration in which the bending portion can be bent in four directions including right and left directions in addition to the up and down directions (that is, bendable in the whole circumferential direction around an axis of the insertion portion by performing different operations for bending the bending portion in the respective up, down, right and left directions (UP, DOWN, RIGHT, and LEFT)).

The flexible tube portion 8 is a tubular member formed to have pliability so as to be passively flexible. The flexible tube portion 8 includes inside thereof a treatment instrument insertion channel (to be described later). In addition, various signal lines extended from the image pickup unit incorporated in the distal end portion 6 and further extended into the universal cord 4 through the inside of the operation portion 3, a light guide (not shown) configured to guide the light emitted from a light source apparatus (not shown) as an external device to an illumination window (not shown) provided on the distal end surface of the distal end portion 6, and the like are inserted through the inside of the flexible tube portion 8.

Note that the light source may be configured as a light emitter (for example, a light-emitting diode: LED) provided inside the operation portion. In such a configuration, the above-described light guide (not shown) is used for guiding the light emitted from the LED in the operation portion to the illumination window of the distal end portion 6. In addition, as an alternative configuration, a light emitter such as an LED may be provided inside the distal end portion 6, at a position close to the proximal end of the illumination window, for example. In such a configuration, the light emitted from the LED passes directly through the illumination window to illuminate the front of the distal end portion 6. Therefore, in such a configuration, there is no need for providing the light guide (not shown) inside the flexible tube portion 8. However, a power supply line for causing the LED provided in the distal end portion 6 to emit light is inserted in the flexible tube portion 8.

The operation portion 3 is a constituent unit provided so as to be continuous with the proximal end portion of the insertion portion 2, and including a plurality of operation members and the like. The operation portion 3 includes a break-prevention portion 9, a grasping portion 10, a plurality of operation members (13, 14, etc.), a treatment instrument insertion portion 11, a suction valve 15, and the like.

The break-prevention portion 9 is provided at a part connecting the distal end portion of the operation portion 3 and the proximal end portion of the flexible tube portion 8. The break-prevention portion 9 is a protection member that covers the proximal end portion of the flexible tube portion 8, to thereby prevent the flexible tube portion 8 from being broken unnecessarily and suddenly during the use of the endoscope 1.

The grasping portion 10 is a housing portion in which various constituent members are housed. The grasping portion 10 is provided so as to be continuous with the break-prevention portion 9. The grasping portion 10 is a part to be grasped by the hand of the user, when the endoscope 1 is used.

The plurality of operation members are provided on the outer surface of the grasping portion 10 and used for operation of various functions of the endoscope 1. The plurality of operation members includes, for example, the bending lever 13 for performing bending operation of the bending portion 7, and in addition, operation members for performing air/water feeding operation and suction operation, and an operation member 14 for performing operations associated respectively to the image pickup unit and illumination unit, etc.

The treatment instrument insertion portion 11 is a constituent part including a treatment instrument insertion port (not shown) through which various treatment instruments (not shown) are inserted, and a treatment instrument insertion path communicating with the treatment instrument insertion channel inside the operation portion 3. Note that the treatment instrument insertion portion 11 is provided with a forceps plug 12 which is a lid member for opening and closing the treatment instrument insertion port and which is configured to be attachable and detachable (exchangeable) with respect to the treatment instrument insertion portion 11.

Note that a suction valve 15 is a linking portion for linking a suction conduit with a suction apparatus, not shown.

The universal cord 4 is a hollow tubular member having flexibility and extending from the operation portion 3. The universal cord 4 is a composite cable in which various signal lines passed through the inside of the insertion portion 2 from the distal end portion 6 of the insertion portion 2, and extended through the inside of the operation portion 3, the light guide extending from the light source apparatus (not shown) as an external device, an air/water feeding tube extending from an air/water feeding apparatus (not shown) as an external device, and the like are inserted.

The endoscope connector 5 is a connecting member disposed at the distal end of the universal cord 4 and ensuring the connection between the endoscope and the external devices. The endoscope connector 5 includes, on a side surface portion thereof, an electric connector portion 16 to which a signal cable connecting the endoscope and a video processor (not shown) as an external device is connected. In addition, the endoscope connector 5 includes a light source connector portion 17 to which a light guide bundle connecting the endoscope and the light source apparatus (not shown) as the external device and an electric cable (not shown) formed by putting the various signal lines together are connected, and an air/water feeding plug 18 to which the air/water feeding tube (not shown) extending from the air/water feeding apparatus (not shown) as the external device is connected.

Figure 2:
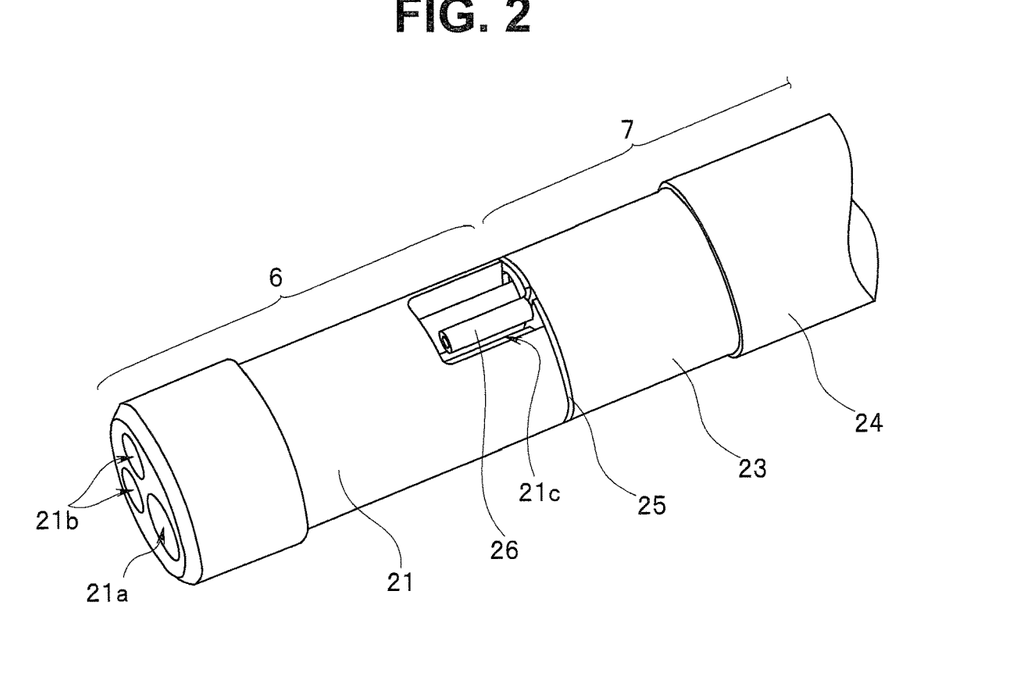
FIG. 2 is a main-part enlarged perspective view showing, in an enlarged manner, a vicinity of a distal end portion (distal end portion and a distal end side of a bending portion) of an insertion portion of the endoscope in FIG. 1.
Figure 3:
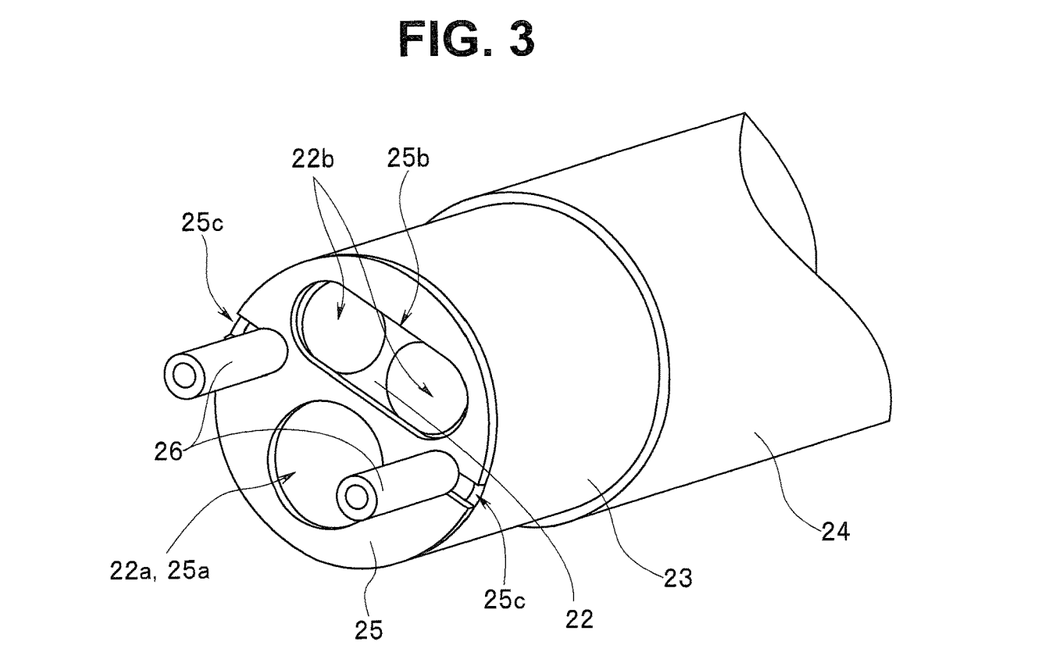
FIG. 3 is a main-part enlarged perspective view showing a state where a distal end rigid member is removed from a configuration of the vicinity of the distal end portion shown in FIG. 2 and an attaching state of bending operation wires at a distal end part of the bending portion.
Figure 4:
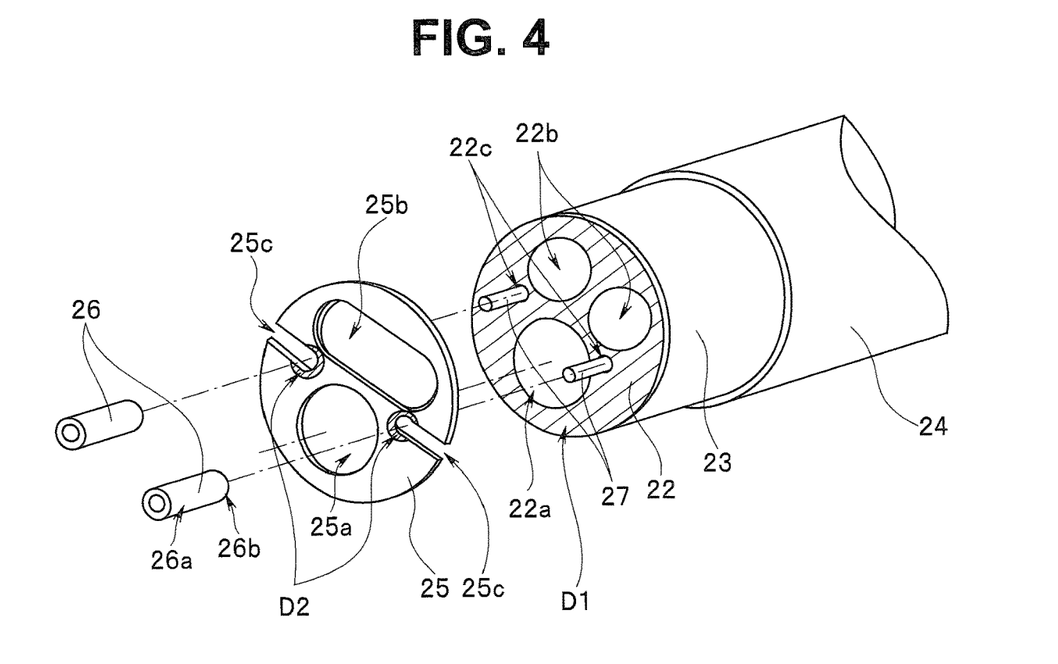
FIG. 4 is an exploded perspective view of FIG. 3.

Next, referring to FIGS. 2 to 4, description will be made below on a detailed configuration of the distal end part of the insertion portion 2 of the endoscope 1 according to the present embodiment. FIG. 2 is a main-part enlarged perspective view showing, in an enlarged manner, a vicinity of the distal end portion (distal end portion and a distal end side of a bending portion) of the insertion portion of the endoscope according to the present embodiment. FIG. 3 is a main-part enlarged perspective view showing a state where a distal end rigid member is removed from the configuration of the vicinity of the distal end portion shown in FIG. 2 and an attaching state of bending operation wires at the distal end part of the bending portion. FIG. 4 is an exploded perspective view of FIG. 3.

Note that, in FIGS. 2 to 4, a part of illustrations of the constituent members which are not related to the present invention is appropriately omitted in order to avoid complexity of the drawings and to clearly illustrate the configurations related to the gist of the present invention. Specifically, a part of an exterior resin member (outer cover member) covering the outer surfaces of the distal end rigid member and the bending portion is omitted, for example.

The distal end portion 6 of the insertion portion 2 is configured by a distal end rigid member 21 (shown only in FIG. 2) which is a rigid frame member made of metal, rigid resin, or the like, for example, and formed in a substantially columnar shape. The distal end rigid member 21 includes, on the distal end surface thereof, an opening portion 21a of a through hole communicating with the treatment instrument insertion channel, an observation window and illumination window (hereinafter shortly referred to as observation illumination window) 21b.

In addition, the distal end rigid member 21 includes, inside thereof, an image pickup unit or an observation unit such as an image guide fiber, and in addition, an illumination unit (none of the units are shown), for example. Therefore, the observation illumination window 21b seals the opening of the through hole communicating with a cable insertion path (not shown) formed so as to pass through the insertion portion 2.

In addition, the distal end rigid member 21 includes, at the proximal end portion thereof, a cut-out window 21c through which the vicinity of the wire attaching portion, to be described later, is exposed. In FIG. 2, only one cut-out window 21c is shown. However, since two wire attaching portions are provided in the present embodiment as described later, two cut-out windows 21c are provided so as to correspond to the two wire attaching portions, respectively. For example, the cut-out window that is not shown in FIG. 2 is provided at a position opposed to the cut-out window 21c shown in FIG. 2 in a radial direction across the longitudinal axis of the distal end rigid member 21.

Note that the configuration of the distal end rigid member 21 itself is substantially the same as the configuration of the distal end rigid member in the conventional endoscope. Therefore, the detailed description on the configuration of the distal end rigid member itself will be omitted.

The bending portion 7 is provided so as to be continuous with the proximal end of the distal end rigid member 21 (see FIGS. 1 and 2). In the endoscope 1 according to the present embodiment, the bending portion 7 is configured by a multi-lumen tube 22 (see FIGS. 3 and 4, not shown in FIGS. 1 and 2), for example.

The multi-lumen tube 22 is a tubular member in which a plurality of hole portions are formed so as to pass through the tubular member in the direction of the longitudinal axis. As shown in FIG. 4, the plurality of hole portions formed in the multi-lumen tube 22 include, for example, a treatment instrument insertion channel hole 22a in which a treatment instrument and the like are inserted, wire insertion holes 22b in which an image pickup signal cable or an image guide fiber, and a light guide fiber, etc., are inserted and arranged, and bending operation wire insertion holes (there are two in the present embodiment) 22c in which bending operation wires 27 (see FIG. 4) are inserted, respectively. Note that each of the bending operation wire insertion holes 22c is formed so as to have a diameter slightly larger than a diameter of each of the bending operation wires 27 to be inserted in the bending operation wire insertion holes, respectively.

As the multi-lumen tube 22, for example, the one formed by using a pliable material such as expanded porous PTFE (ePTFE: expanded PTFE) formed by performing expanding processing on PTFE (polytetrafluoroethylene) which is one type of fluorine resin is applied.

The outer surface of the multi-lumen tube 22 is covered with, for example, a braid layer 23 which is a mesh tube. The outer surface of the braid layer 23 is further covered with an exterior resin member (outer cover) 24. The exterior resin member 24 covers the outer surfaces of the bending portion 7 and the flexible tube portion 8 (see FIG. 1) from the part close to the proximal end of the distal end rigid member 21.

A wire retaining member 25 is held between the distal end rigid member 21 and the multi-lumen tube 22. The wire retaining member 25 is configured to retain the distal ends of the bending operation wires 27, and includes at least hole portions 25c serving as opening portions from which the bending operation wires 27 (see FIG. 4) are drawn out, respectively. The wire retaining member 25 is in contact with the distal end surface of the multi-lumen tube 22 in a watertight manner, and is also in contact with the proximal end surface of the distal end rigid member 21 in a watertight manner.

The wire retaining member 25 is a substantially circular-shaped plate member formed so as to be substantially the same shape as the cross-sectional shape of the multi-lumen tube 22. The wire retaining member 25 is formed by using a sufficiently rigid material.

Specifically, the wire retaining member 25 is a metal part formed by press processing of a plate metal member, or a resin molded part formed by injection molding of a resin material, for example.

The wire retaining member 25 includes holes (25a, 25b, 25c) corresponding respectively to the plurality of holes (22a, 22b, 22c) of the multi-lumen tube 22.

In the configuration, the first hole portion 25a of the wire retaining member 25 is a through hole corresponding to the treatment instrument insertion channel hole 22a of the multi-lumen tube 22. The first hole portion 25a is formed in a circular shape which is substantially the same shape as the shape of the treatment instrument insertion channel hole 22a and which has a diameter substantially the same as or slightly larger than the diameter of the treatment instrument insertion channel hole 22a.

Similarly, the second hole portion 25b of the wire retaining member 25 is a through hole corresponding to the wire insertion holes 22b of the multi-lumen tube 22. The second hole portion 25b is formed in a substantially oval shape so as to correspond to the plurality of (two) wire insertion holes 22b and to allow the plurality of (two) wire insertion holes 22b to be exposed together. In the configuration, the length of the short axis of the oval shape of the second hole portion 25b is substantially the same or slightly greater than the length of the diameter of each of the wire insertion holes 22b.

In the present embodiment, the second hole portion 25b is formed in the substantially oval shape. However, the shape of the second hole portion 25b is not limited to the oval shape, but the second hole portion 25b may be formed as holes corresponding respectively to the plurality of (two) wire insertion holes 22b and having the same shapes and diameters as those of the respective wire insertion holes 22b, for example.

Similarly, the third hole portions 25c of the wire retaining member 25 are through holes corresponding respectively to the plurality of (two) bending operation wire insertion holes 22c of the multi-lumen tube 22. Each of the third holed portions 25c has a width dimension slightly larger than the diameter of each of the bending operation wire insertion holes 22c, and is formed in a cut-out shape which is cut from the outer peripheral edge portion in the radial direction.

Note that the two third hole portions 25c are provided at positions corresponding respectively to the two bending operation wire insertion holes 22c. That is, the two third hole portions 25c are provided at the positions opposed to each other in the radial direction across the longitudinal axis of the multi-lumen tube 22. That is, the two third hole portions 25c are arranged at the positions corresponding to the respective cut-out windows 21c of the distal end rigid member 21 when the endoscope 1 is in the assembled state.

Thus, the cut-out windows 21c are provided at the distal end rigid member 21 and the cut-out shaped third hole portions 25c of the wire retaining member 25 are provided at the positions corresponding respectively to the cut-out windows 21c, to thereby enable the endoscope 1 according to the present embodiment to contribute to the improvement of workability when the bending operation wires 27 are fitted.

In the present embodiment, the example in which the third hole portions 25c are formed in the cut-out shape is shown, but the present invention is not limited to the example. For example, each of the third hole portions 25c may be formed as a hole having the same shape as that of each of the (two) bending operation wire insertion holes 22c so as to correspond to each of the bending operation wire insertion holes 22c. In the configuration, the hole diameter of each of the third hole portions 25c has only to be formed to be slightly larger than the diameter of each of the bending operation wire insertion holes 22c.

As described above, the bending operation wires 27 inserted and arranged respectively in the plurality of (two) bending operation wire insertion holes 22c of the multi-lumen tube 22 are arranged such that the distal ends of the bending operation wires are protruded outside (forward) respectively from the bending operation wire insertion holes 22c. At this time, the other ends of the respective bending operation wires 27 are inserted through the insertion portion 2 and coupled to the bending operation mechanism (not shown) in the operation portion 3.

The respective distal ends of the bending operation wires 27, which are protruded outside (forward) from the bending operation wire insertion holes 22c, are further inserted into the respective third hole portions 25c of the wire retaining member 25, to be protruded to the front surface side of the wire retaining member 25. At the protruded parts of the respective distal ends of the bending operation wires 27, pressing members 26, which serve as wire tip members and as wire stopping members, are fixed.

The pressing members 26 are formed by swaging (compression molding) of pipe members, for example, and fixed to the respective distal ends of the bending operation wires 27. Each of the pressing members 26 is formed such that the diameter or the width dimension in a direction orthogonal to the longitudinal axis direction is larger (diameter) than the cut-out width (or diameter) of each of the third hole portions 25c of the wire retaining member 25.

With such a configuration, each of the bending operation wires 27 inserted from the third hole portion 25c into the bending operation wire insertion hole 22c is retained, with each of the pressing members 26 fixed to each of the distal ends of the bending operation wires 27 being in contact with a portion around each of the third hole portions 25c of the wire retaining member 25. With such a configuration, each of the pressing member 26 is configured to be capable of receiving the pulling force of each of the bending operation wires 27.

In this embodiment, each of the parts fixed to the distal ends of the bending operation wires 27 is referred to as a fixation portion 26a (see FIG. 4) of each of the pressing members 26. In addition, similarly, each of the parts which is in contact with the wire retaining member 25 is referred to as a contact portion 26b of each of the pressing members 26. That is, the pressing members 26 are formed by respectively including fixation portions 26a fixed to the bending operation wires 27 and the contact portions 26b which are in contact with the wire retaining member 25.

With such a configuration, when a predetermined operation member is operated by a user and one of the bending operation wires 27 is pulled, for example, the pressing member 26 of the pulled bending operation wire 27 presses the distal end surface of the multi-lumen tube 22 through the wire retaining member 25.

The contact area (see the reference sign D1 in FIG. 4; the part indicated with the hatched lines) of the wire retaining member 25 with the distal end surface of the multi-lumen tube 22 is set to be larger than the contact area (see the reference sign D2; the part indicated with the hatched lines) of each of the contact portions 26b of the pressing members 26 with the wire retaining member 25.

With such a configuration, when the contact portion 26b of the pressing member 26 of the pulled bending operation wire 27 presses the wire retaining member 25 by the pulling force generated when the bending operation wires 27 is pulled, the pulling force applied to the contact portion 26b of the pressing member 26 is diverged by the wire retaining member 25, to thereby cause the pressing member 26 to press the distal end surface (see the reference sign D1 in FIG. 4) of the multi-lumen tube 22 evenly. Therefore, the pressing members 26 does not deform the pliable multi-lumen tube 22.

Note that, in the above-described first embodiment, the pressing members 26 are formed by swaging (compression molding) of the pipe members and fixed to the respective distal ends of the bending operation wires 27. However, the configuration of the pressing members 26 is not limited to the example as described above. The pressing members 26 have only to be formed in a shape so as to be retained in the third hole portions 25c of the wire retaining member 25. Therefore, as another configuration of the pressing members 26, when the pipe members are fixed to the distal ends of the bending operation wires 27, the pipe members may be fixed, for example, by brazing, soldering, adhering with adhesive, or the like, other than the above-described swaging. Furthermore, bending operation wires 27 including ball-shaped members fixed to one end portions (distal ends) thereof in advance may be used.

As described above, according to the first embodiment, when the distal end parts of the bending operation wires 27 are fixed at the distal end part of the bending portion 7, the plate-shaped wire retaining member 25 is provided so as to be held between the distal end surface of the multi-lumen tube 22, which constitutes the bending portion 7, and the proximal end surface of the distal end rigid member 21, and the pressing members 26 are fixed to the distal ends of the bending operation wires 27.

With such a configuration, when the pulling operation of one of the bending operation wires 27 is performed, the pulling force of the pulled bending operation wires 27 acts so as to cause the contact portion 26b of the pressing member 26 of the pulled bending operation wire 27 to contact the wire retaining member 25, to thereby press the wire retaining member 25 against the distal end surface of the multi-lumen tube 22.

The contact area (see the reference sign D1 in FIG. 4) of the wire retaining member 25 with the distal end surface of the multi-lumen tube 22 is set to be sufficiently larger than the contact area (see the reference sign D2 in FIG. 4) of each of the contact portions 26b of the pressing members 26 with the wire retaining member 25, which prevents the multi-lumen tube 22 from being deformed by the pulling force of the pulled bending operation wires 27.

Therefore, the above-described configuration is capable of suppressing the functional disorders (for example, variations in the bending angle and the bending operation feeling) of the bending portion 7 to be caused by the deformation of the multi-lumen tube 22, to thereby be capable of maintaining the accuracy of the bending angle, and ensuring always stable operation feeling.

In addition, in the present embodiment, the wire retaining member 25 has a simple plate shape. That is, the wire retaining member 25 can be easily manufactured in large quantities in a short time at a low cost by metal stamping or injection molding, for example. Therefore, the present embodiment can contribute to the reduction in the manufacturing cost.

Note that the first embodiment shows the example in which the two bending operation wires are provided. However, the number of the bending operation wires is not limited to the above-described example. For example, in the endoscope according to the second embodiment of the present invention, which is to be described next, an example in which one bending operation wire is provided is shown.

Second Embodiment

Figure 5:
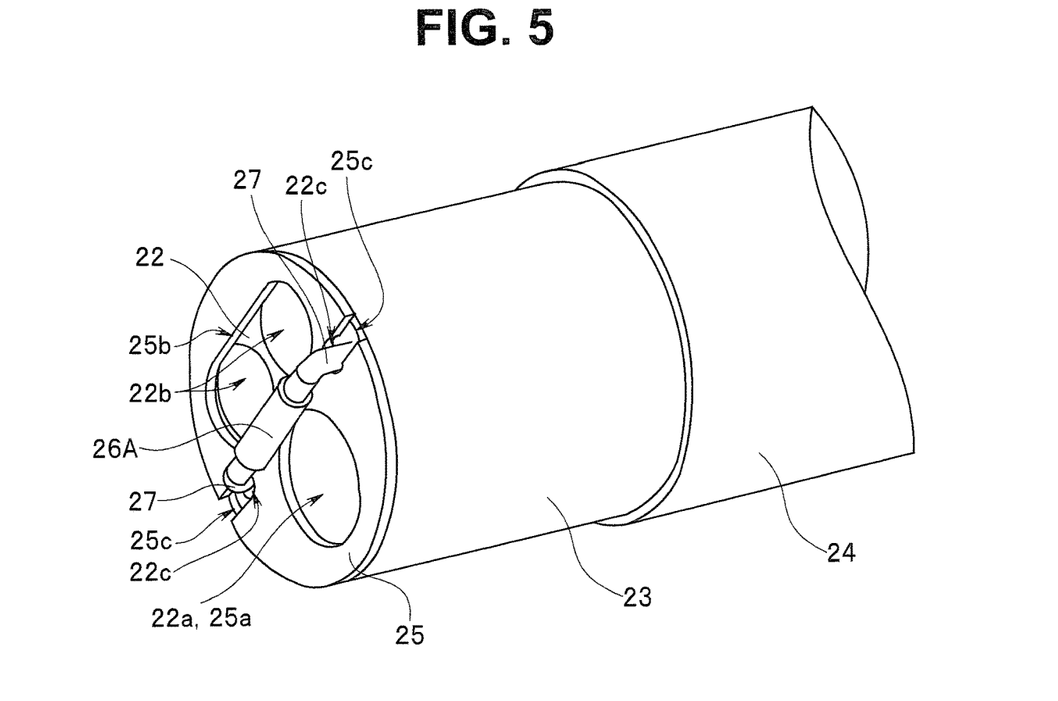
FIG. 5 is a main-part enlarged perspective view showing a configuration of a distal end part of a bending portion of an insertion portion of an endoscope according to a second embodiment of the present invention, and showing, in particular, an attaching state of a bending operation wire.

The endoscope according to the second embodiment of the present invention will be described below with reference to FIG. 5. FIG. 5 is a main-part enlarged perspective view showing the configuration of the distal end part of the bending portion of the insertion portion of the endoscope according to the second embodiment of the present invention, and showing, in particular, the attaching state of the bending operation wire.

The present embodiment has configurations basically and substantially same as those in the first embodiment, but is different from the first embodiment only in that one bending operation wire is provided, which creates a difference in attaching means for attaching the bending operation wire to the distal end part of the bending portion. Other configurations are substantially the same as those in the first embodiment. Therefore, in the description below, only the part different from that in the first embodiment will be described, and the same constituent elements as those in the first embodiment will be attached with the same reference signs and descriptions thereof will be omitted.

In the endoscope according to the present embodiment, the one bending operation wire 27 is used to enable the bending operation in two directions, that is, either up and down directions or left and right directions.

That is, one end of the bending operation wire 27 is inserted into one of the third hole portions 25c and one of the bending operation wire insertion holes 22c, and the other end of the bending operation wire 27 is inserted into the other of the third hole portions 25c and the other of the bending operation wire insertion holes 22c. The bending operation wire 27 is arranged, with the middle part thereof which forms a loop shape exposed outside (forward) of the wire retaining member 25.

In other words, the multi-lumen tube 22 includes the two bending operation wire insertion holes 22c that pass through the multi-lumen tube in the direction of the longitudinal axis. In this embodiment, one of the bending operation wires insertion holes 22c is simply referred to as the bending operation wire insertion hole 22c, and the other of the bending operation wire insertion holes 22c is referred to as a second bending operation wire 22c.

In the present embodiment, the bending operation wire 27 is inserted into the one of the bending operation wire insertion holes 22c, and the one end of the bending operation wire 27 reaches the bending operation mechanism (not shown) of the operation portion 3. In addition, the other end of the bending operation wire 27 passes through the bending operation wire insertion hole 22c of the multi-lumen tube 22 to be protruded outside from one of the third hole portions 25c of the wire retaining member 25, and further extended to be inserted into the second bending operation wire insertion hole 22c. The other end of the bending operation wire 27 reaches the bending operation mechanism (not shown) of the operation portion 3. With such a configuration, the middle part of the bending operation wire 27 forms a loop shape to be exposed outside from the two bending operation wire insertion holes 22c and the two third hole portions 25c.

Furthermore, the loop-shaped part of the bending operation wire 27 is bent at the positions in the vicinity of the opening portions of the two third hole portions 25c, and a predetermined bending habit is applied to the loop-shaped part. This allows the bending operation wire 27 to be retained by the wire retaining member 25.

In the present embodiment, the loop-shaped part located at the middle part of the bending operation wire 27 is provided with a pressing member 26A configured by a pipe member. The pressing member 26A is fixed to a position bridging the two third hole portions 25c on the front surface of the wire retaining member 25.

In the configuration, the pressing member 26A fixed to the bending operation wire 27 by being swaged (press-molded) at the loop-shaped part of the bending operation wire 27. Furthermore, the pressing member 26A is fixed to a predetermined part on the front surface of the wire retaining member 25 so as to prevent the pressing member 26A from moving in one direction when the pulling operation of the bending operation wire 27 is performed. In this embodiment, the fixation of the pressing member 26A to the front surface of the wire retaining member 25 may be performed by brazing, soldering, adhesion by using adhesive, and the like, for example. Other configurations are substantially the same as those in the first embodiment.

The second embodiment thus configured is also capable of obtaining substantially the same effects as those in the first embodiment.

Note that the present embodiment shows the exemplary configuration in which the one bending operation wire 27 is provided. However, the number of the bending operation wire is not limited to one. Even in the case where the two bending operation wires 27 are provided, the same configuration can be applied.

That is, the respective end portions of the two bending operation wires 27 are inserted through the respective third hole portions 25c and the bending operation wire insertion holes 22c, while the respective distal end portions of the two bending operation wires 27 are protruded from the respective third hole portions 25c to the outside (forward) of the wire retaining member 25. In this state, the respective distal end portions of the bending operation wires 27 are connected to each other by using the pressing member 26A which is a pipe member. According to such a configuration, the endoscope including the two bending operation wires 27 can be configured in exactly the same manner as the second embodiment. The working and effects in such a configuration are identical to those in the second embodiment.

Third Embodiment

Incidentally, a common medical endoscope is configured to perform a desired treatment by inserting a treatment instrument and the like into a treatment instrument insertion channel of an insertion portion of the endoscope in the state where the insertion portion is inserted into a body cavity of a subject and by causing the distal end part of the treatment instrument to protrude into the body cavity. In this case, since the endoscope is used in an ambient environment in which liquids such as body fluid, cleaning solution, and the like exist. There is a possibility that a reflux liquid and the like flow from the distal end opening portion into the treatment instrument insertion channel. Therefore, the vicinity of the distal end portion of the endoscope is configured to have a watertight structure.

In the above-described first and second embodiments, the plate-shaped wire retaining member 25 is held between the distal end surface of the bending portion 7 (multi-lumen tube 22) and the proximal end surface of the distal end rigid member 21, to thereby bring the distal end surface of the bending portion and the proximal end surface of the distal end rigid member into contact with each other in a watertight manner. In addition, the treatment instrument insertion channel passes through the part connecting the bending portion 7 (multi-lumen tube 22) and the distal end rigid member 21, and is formed so as to reach the distal end surface of the distal end rigid member 21.

In such a configuration, when the diameter of the treatment instrument insertion channel is set to be larger than the diameter of the endoscope, there is a case where the thickness around the treatment instrument insertion channel at the part connecting the bending portion 7 (multi-lumen tube 22) and the distal end rigid member 21 becomes thin.

As in the configurations in the first and second embodiments, if the part connecting the bending portion 7 (multi-lumen tube 22) and the distal end rigid member 21 is configured by the planes contacting with each other, there is a case where it is difficult to surely secure the water-tightness between the bending portion and the distal end rigid member due to various factors such as deterioration over time.

In view of the above-described problem, the third embodiment of the present invention, which is to be described next, is configured so as to be capable of surely securing the water-tightness between the distal end rigid member and the bending portion by contriving the configuration of the part connecting the bending portion (multi-lumen tube) and the distal end rigid member, in particular, the wire retaining member.

Figure 6:
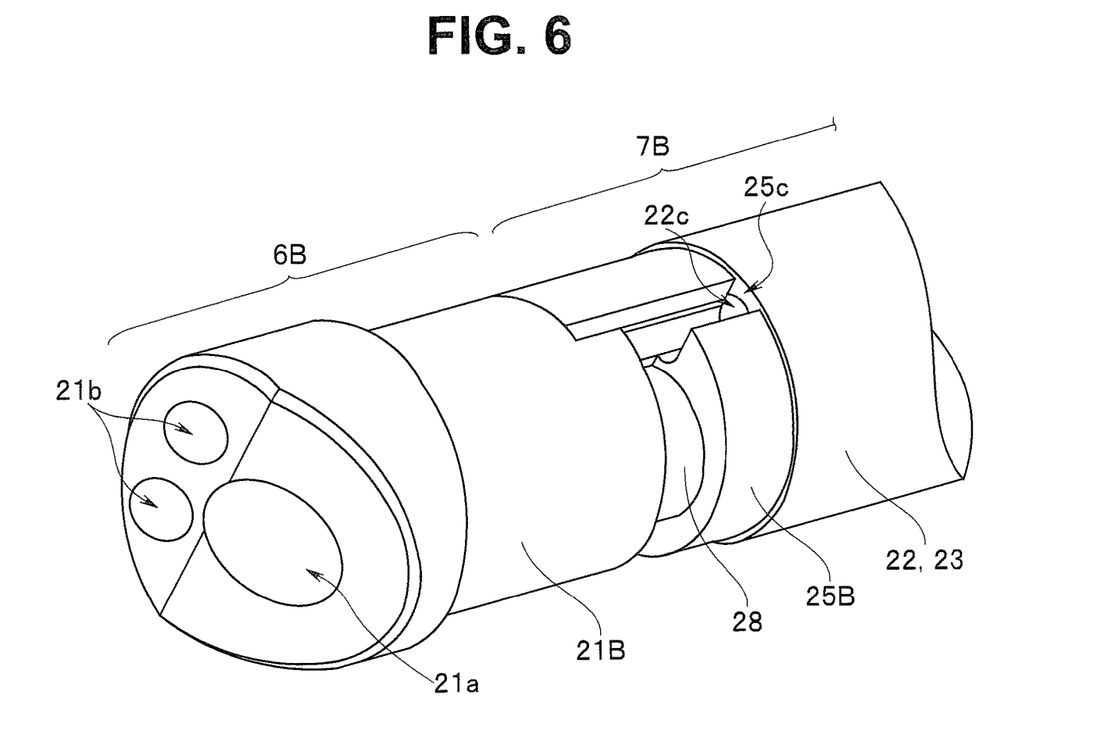
FIG. 6 is a main-part enlarged perspective view showing, in an enlarged manner, a vicinity of a distal end portion (distal end portion and a distal end side of a bending portion) of an insertion portion of an endoscope according to a third embodiment of the present invention.
Figure 7:
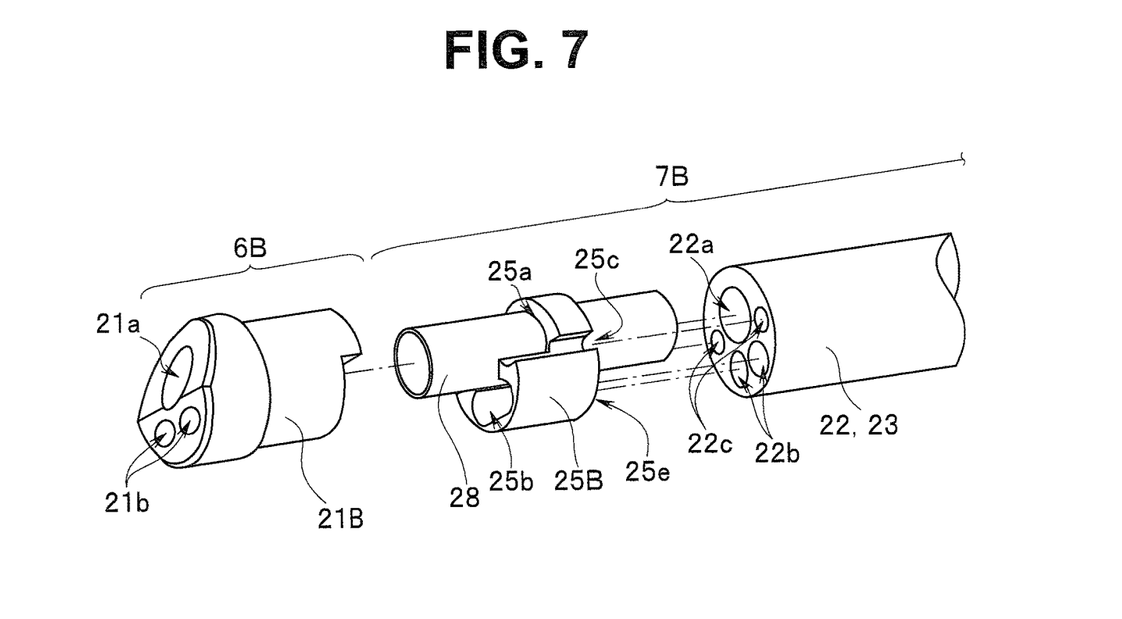
FIG. 7 is an exploded perspective view of FIG. 6.
Figure 8:
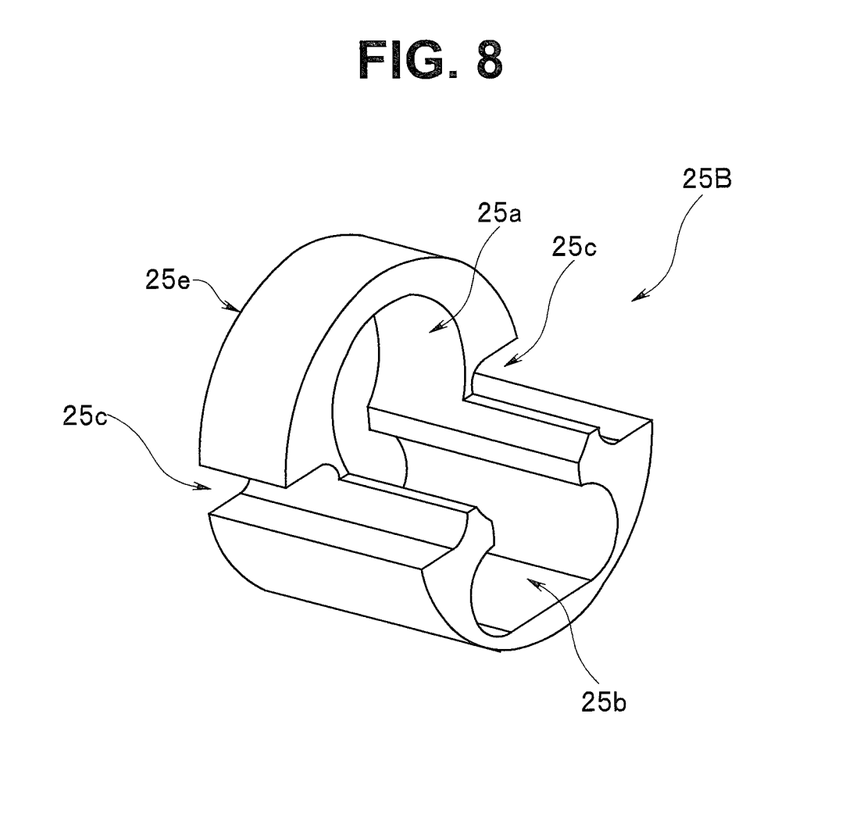
FIG. 8 is an enlarged perspective view showing a wire retaining member by taking out only the wire retaining member from constituent members of the endoscope according to the third embodiment.
Figure 9:
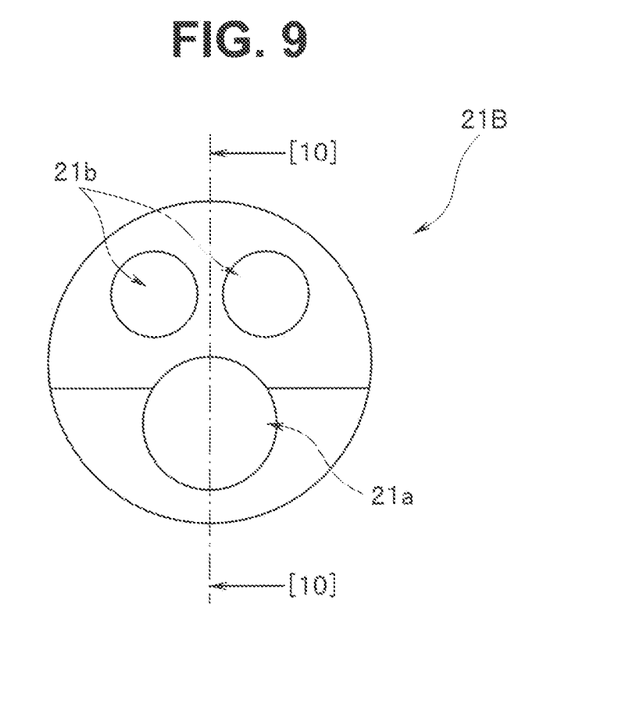
FIG. 9 is a plan view showing a distal end rigid member of the endoscope, which is viewed from the front, according to the third embodiment.
Figure 10:
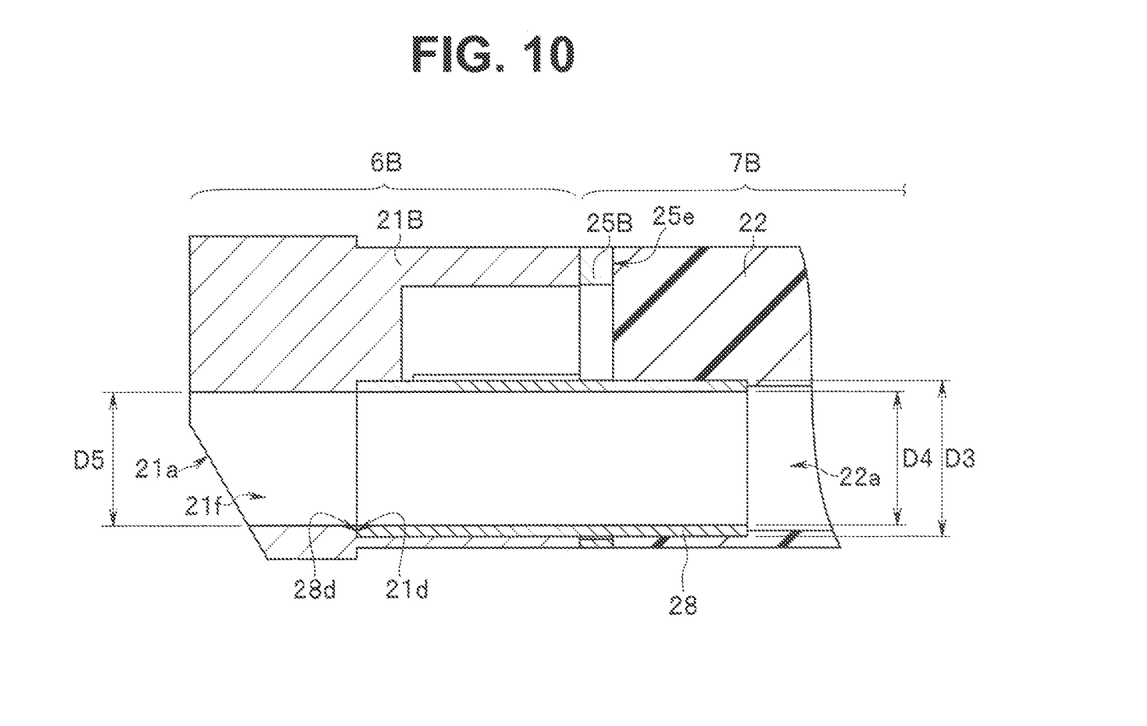
FIG. 10 is a vertical cross-sectional view taken along the line [10]-[10] in FIG. 9.

Hereinafter, description will be made on the endoscope according to the third embodiment of the present invention, with reference to FIGS. 6 to 10. FIG. 6 is a main-part enlarged perspective view showing, in an enlarged manner, the vicinity of the distal end portion (distal end portion and the distal end side of a bending portion) of the insertion portion of the endoscope according to the third embodiment of the present invention. FIG. 7 is an exploded perspective view of FIG. 6. FIG. 8 is an enlarged perspective view showing the wire retaining member by taking out only the wire retaining member from the constituent members shown in FIGS. 6 and 7. FIG. 9 is a plan view showing the distal end rigid member shown in FIGS. 6 and 7, which is viewed from the front. FIG. 10 is a vertical cross-sectional view taken along the line [10]-[10] in FIG. 9.

Note that, in FIGS. 6 to 10, illustrations of the constituent members which are not related to the present invention are appropriately omitted in order to avoid complexity of the drawings. In addition, in FIG. 7, FIG. 10, etc., illustration of the bending operation wire is also omitted.

Also the configuration in the present embodiment are substantially the same as the configurations of the first and second embodiments, but the present embodiment is different from the first and second embodiments only in the configuration of the part (the wire retaining member, etc., in particular) connecting the bending portion (multi-lumen tube) and the distal end rigid member. Therefore, in the configuration of the present embodiment, the same constituent elements as those in the above-described first and second embodiments are attached with the same reference signs and detailed descriptions thereof will be omitted. Only the different part will be detailed.

In the endoscope according to the present embodiment, the vicinity of the distal end portion is configured by a distal end portion 6B and a bending portion 7B as shown in FIGS. 6 and 7, etc.

The distal end portion 6B is configured by a distal end rigid member 21B. In the present embodiment, the distal end rigid member 21B is slightly different only in the shape thereof from the distal end rigid member 21 in the first and second embodiments, but the basic configuration of the distal end rigid member 21B is the same as that of the distal end rigid member 21.

That is, the distal end rigid member 21B is formed in a substantially columnar shape and includes, on the distal end surface thereof, an opening portion 21a of a through hole 21f (see FIG. 10 to be described later) communicating with the treatment instrument insertion channel and an observation illumination window 21b which serves as an opening of the through hole communicating with the cable insertion path (not shown) of the insertion portion 2.

The bending portion 7B is configured by the multi-lumen tube 22 similarly as the bending portion 7 in the first and second embodiments. The outer surface of the multi-lumen tube 22 is covered with a braid layer 23, for example.

The multi-lumen tube 22 is configured by including a treatment instrument insertion channel hole 22a as the treatment instrument insertion channel that passes through the multi-lumen tube 22 in the direction of the longitudinal axis. The treatment instrument insertion channel hole 22a extends toward the proximal end side with respect to a wire retaining member 25B to be described later.

The wire retaining member 25B is provided so as to be held between the bending portion 7B (multi-lumen tube 22) and the distal end rigid member 21B, to connect the bending portion and the distal end rigid member in a watertight manner.

As shown in FIGS. 6 to 8, etc., the wire retaining member 25B is a part formed in a substantially cylindrical shape as a whole, and configured to retain the end portion of the bending operation wire 27 (not shown) and play a role for suppressing the deformation of the multi-lumen tube 22 due to the pulling force of the bending operation wire 27.

To this end, the wire retaining member 25B includes a plane portion 25e that is in contact with the distal end surface of the multi-lumen tube 22, a first hole portion 25a corresponding to the treatment instrument insertion channel hole 22a of the multi-lumen tube 22 and the opening portion 21a of the distal end rigid member 21, a second hole portion 25b corresponding to the wire insertion holes 22b of the multi-lumen tube 22 and the observation illumination window 21b of the distal end rigid member 21, and third hole portions 25c each having a cut-out shape, which correspond to the bending operation wire insertion holes 22c of the multi-lumen tube 22.

In addition, on the distal end side of the wire retaining member 25B, the distal end rigid member 21B including the through holes is provided. In this configuration, the through holes of the distal end rigid member 21B correspond to the opening portion 21a and the observation illumination window 21b and communicate respectively with the treatment instrument insertion channel holes 22a and the wire insertion holes 22b, similarly as in the first and second embodiments.

A pipe member 28 made of a rigid material and formed in a substantially cylindrical shape is held in the first hole portion 25a of the wire retaining member 25B. Thus, the first hole portion 25a functions as a pipe holding portion that holds the pipe member 28.

One end of the pipe member 28 is inserted into the treatment instrument insertion channel hole 22a. Therefore, the pipe member 28 is formed so as to have a diameter substantially the same or slightly larger than the diameter of the treatment instrument insertion channel hole 22a.

Therefore, when the one end of the pipe member 28 is inserted in the treatment instrument insertion channel hole 22a of the multi-lumen tube 22, the pipe member 28 is press-fitted by pushingly enlarging the treatment instrument insertion channel hole 22a by the pipe member 28. The multi-lumen tube 22 is made of a pliable material. Therefore, when the pipe member 28 made of a rigid material is inserted into the multi-lumen tube 22, the treatment instrument insertion channel hole 22a is stretched to cover the outer surface of the pipe member 28. When the one end of the pipe member 28 is thus inserted into the treatment instrument insertion channel hole 22a of the multi-lumen tube 22, a watertight structure is formed between the pipe member and the multi-lumen tube.

On the other hand, the other end of the pipe member 28 is inserted into the through hole 21f (see FIG. 10) of the distal end rigid member 21B. In the present embodiment the through hole 21f of the distal end rigid member 21B is a through hole corresponding to the treatment instrument insertion channel hole 22a. The through hole 21f is formed so as to have a diameter slightly larger than the outer diameter D3 of the pipe member 28, to thereby allow easy insertion of the pipe member. In addition, on the distal end side of the through hole 21f, a step portion 21d (see FIG. 10) with which the distal end surface 28d of the inserted pipe member 28 is in contact is formed (see FIG. 10). That is, the inner diameter D5 of the step portion 21d is formed to be smaller than the outer diameter D3 of the pipe member 28 (D3>D5). With such a configuration, when the other end of the pipe member 28 is inserted into the distal end rigid member 21B, the position of the pipe member 28 is restricted by the distal end surface 28d of the pipe member 28 being in contact with the step portion 21d.

Furthermore, the step portion 21d is formed such that the inner diameter D5 thereof is substantially the same as the inner diameter D4 of the pipe member 28. With such a configuration, when the other end of the pipe member 28 is inserted into the through hole 2 if of the distal end rigid member 21B and the one end of the pipe member 28 is inserted into the treatment instrument insertion channel hole 22a, the treatment instrument insertion channel hole 22a and the through hole 21f of the distal end rigid member 21B communicate with each other. Other configurations are substantially the same as those in the first and second embodiments.

The third embodiment as configured above is also capable of obtaining the same effects as those in the above-described first and second embodiments.

In addition, in the present embodiment, the pipe member 28 is held in the first hole portion 25a of the wire retaining member 25B provided at the part connecting the bending portion 7B (multi-lumen tube 22) and the distal end rigid member 21B. Then, the one end of the pipe member 28 is inserted into the treatment instrument insertion channel hole 22a of the multi-lumen tube 22 of the bending portion 7B. In addition, the other end of the pipe member 28 is inserted into the through hole 21f of the distal end rigid member 21B.

With such a configuration, the water-tightness of the part connecting the bending portion 7B (multi-lumen tube 22) and the distal end rigid member 21 can be surely ensured.

The present invention is not limited to the above-described embodiments, and it is needless to say that various modifications and applications are possible without departing from the gist of the present invention. Furthermore, the above-described embodiments include inventions at various stages, and by appropriately combining a plurality of components disclosed in the embodiments, inventions at various stages can also be extracted. For example, even if some components are deleted from all the components shown in the above-described present embodiments, if the problem to be solved by the invention can be solved and the effects of the invention can be obtained, the configuration in which some components are deleted can be extracted as an invention. In addition, the constituent elements in different embodiments may be appropriately combined. The present invention is not limited by the specific embodiments of it except as limited by the appended claims.

The present invention can be applied not only to endoscope control apparatuses in medical fields but also to endoscope control apparatuses in industrial fields.

What is claimed is:

1. An endoscope comprising:
   an insertion portion configured to be inserted into a subject, the insertion portion including a bending portion;
   a multi-lumen tube that forms at least the bending portion of the insertion portion, the multi-lumen tube including two bending operation wire insertion holes passing through the multi-lumen tube in a direction of a longitudinal axis;
   two bending operation wires inserted respectively into the two bending operation wire insertion holes;
   a wire retaining member in contact with a distal end surface of the multi-lumen tube, the wire retaining member including two opening portions from which the two bending operation wires are respectively drawn out;
   a pressing member including a fixation portion fixed to the two bending operation wires and a contact portion in contact with the wire retaining member, the pressing member being configured to press a distal end surface of the multi-lumen tube through the wire retaining member when one of the two bending operation wires is pulled;
   a treatment instrument insertion channel provided on a proximal end side of the wire retaining member, the treatment instrument insertion channel communicating with the multi-lumen tube in the direction of the longitudinal axis;
   a distal end rigid member provided on a distal end side of the wire retaining member, the distal end rigid member including a through hole; and
   a pipe member including one end inserted into the treatment instrument insertion channel and another end inserted into the through hole of the distal end rigid member, the pipe member being configured to allow the treatment instrument insertion channel and the through hole of the distal end rigid member to communicate with each other,
   wherein,
   a contact area of the wire retaining member with the distal end surface of the multi-lumen tube is set to be larger than a contact area of the contact portion with the wire retaining member,
   the pressing member is disposed between the two opening portions of the wire retaining member,
   the wire retaining member includes a pipe holding portion configured to allow insertion of the pipe member and to hold the pipe member, the wire retaining member being held between the distal end rigid member and the multi-lumen tube, and
   the through hole of the distal end rigid member includes a step portion configured to restrict a position of the pipe member by a distal end surface of the pipe member inserted in the though hole being in contact with the step portion,
   wherein an inner diameter of the step portion is smaller than an outer diameter of the pipe member and the inner diameter of the step portion is substantially equal to an inner diameter of the pipe member.

2. The endoscope according to claim 1, wherein the pressing member is fixed to the wire retaining member.

3. The endoscope according to claim 1, wherein the wire retaining member is configured by a plate-shaped member.

4. The endoscope according to claim 1, wherein the pressing member is a pipe-shaped member having a diameter larger than a diameter of the bending operation wires, and the pipe-shaped member is fixed by caulking to distal end portions of the bending operation wires.

5. The endoscope according to claim 1, wherein end portions of the two wires are connected to each other by the pressing member.

* * * * *